(12) United States Patent
Sekiguchi et al.

(10) Patent No.: US 8,877,493 B2
(45) Date of Patent: Nov. 4, 2014

(54) CULTURE SUBSTRATE FOR HUMAN PLURIPOTENT STEM CELLS AND USE THEREOF

(75) Inventors: Kiyotoshi Sekiguchi, Osaka (JP); Sugiko Futaki, Osaka (JP); Yukimasa Taniguchi, Osaka (JP); Maria Hayashi, Osaka (JP); Norio Nakatsuji, Kyoto (JP); Takamichi Miyazaki, Kyoto (JP); Eihachiro Kawase, Kyoto (JP); Hirofumi Suemori, Kyoto (JP)

(73) Assignees: Osaka University, Osaka (JP); Kyoto University, Kyoto (JP)

( * ) Notice: Subject to any disclaimer, the term of this patent is extended or adjusted under 35 U.S.C. 154(b) by 0 days.

(21) Appl. No.: 13/500,452

(22) PCT Filed: Oct. 7, 2010

(86) PCT No.: PCT/JP2010/067618
§ 371 (c)(1),
(2), (4) Date: May 15, 2012

(87) PCT Pub. No.: WO2011/043405
PCT Pub. Date: Apr. 14, 2011

(65) Prior Publication Data
US 2012/0220031 A1    Aug. 30, 2012

(30) Foreign Application Priority Data
Oct. 8, 2009  (JP) .................. 2009-234583

(51) Int. Cl.
C12N 5/071      (2010.01)
C12N 5/00       (2006.01)
C12N 5/074      (2010.01)
C12N 5/0735     (2010.01)

(52) U.S. Cl.
CPC ............ C12N 5/0606 (2013.01); C12N 5/0696 (2013.01); C12N 2533/52 (2013.01)

USPC ............ 435/366; 435/325; 435/395; 435/402

(58) Field of Classification Search
None
See application file for complete search history.

(56) References Cited

U.S. PATENT DOCUMENTS

| 2005/0158852 A1 | 7/2005 | Wang et al. |
| 2008/0058221 A1* | 3/2008 | Terskikh et al. ................ 506/10 |

(Continued)

FOREIGN PATENT DOCUMENTS

| WO | 2007/023875 | 3/2007 |
| WO | 2008/084401 | 7/2008 |
| WO | 2009/123349 | 10/2009 |

OTHER PUBLICATIONS

Chen et al., Am. J. Physiol., L494-503 (1997).*

(Continued)

*Primary Examiner* — Blaine Lankford
*Assistant Examiner* — Thomas J Visone
(74) *Attorney, Agent, or Firm* — Wenderoth, Lind & Ponack, L.L.P.

(57) ABSTRACT

The present invention provides a culture substrate which enables maintenance culture of human pluripotent stem cells in a pluripotent state under a feeder-free culture environment, and a culture method of human pluripotent stem cells using the culture substrate. By seeding human pluripotent stem cells dissociated into single cells at a cell density of $4 \times 10^4$ to $10 \times 10^4$ cells/cm$^2$ onto a culture substrate coated with human laminin α5β1γ1 E8 fragment or human laminin α3β3γ2 E8 fragment preferably at a concentration of 0.5 to 25 μg/cm$^2$, the human pluripotent stem cells can be rapidly expanded in a pluripotent state.

7 Claims, 5 Drawing Sheets

(56) References Cited

U.S. PATENT DOCUMENTS

2008/0213885 A1    9/2008    Tryggvason et al.
2009/0269848 A1    10/2009    Miyazaki et al.
2010/0203635 A1    8/2010    Tryggvason et al.

OTHER PUBLICATIONS

Drago et al., Exp. Cell Res., 192:256-65, Abstract Only (1991).*
Bajpai et al., Mol. Repro. Dev., 75:818-827 (2008).*
Liu et al., Micro Nanosys., 2:269-273 (2010).*
Li et al., Hum. Repro., 24(3): 580-589 (2009).*
Extended European Search Report issued Mar. 15, 2013 in corresponding European Patent Application No. 10822075.7.
T. Miyazaki et al., "Laminin E8 fragments support efficient adhesion and expansion of dissociated human pluripotent stem cells", Nature Communications, vol. 3, p. 1236, 2012.
Office Action issued Nov. 22, 2013 in corresponding European Application No. 10 822 075.7.
Response filed May 16, 2014 to the Office Action issued Nov. 22, 2013 in corresponding European Application No. 10 822 075.7.
Rowland, et al., "Roles of Integrins in Human Induced Pluripotent Stem Cell Growth on Matrigel and Vitronectin", Stem Cells and Development, 2010, vol. 19, No. 8, pp. 1231-1240.
Phillips et al., "Attachment and growth of human embryonic stem cells on microcarriers", Journal of Biotechnology, 2008, vol. 138, pp. 24-32.
Rodin et al., "Long-term self-renewal of human pluripotent stem cells on human recombinant laminin-511", Nature Biotechnology, Jun. 2010, vol. 28, No. 6, pp. 611-617.
English translation of the International Preliminary Report on Patentability, 2012.
S. Vuoristo et al., "Laminin Isoforms in Human Embryonic Stem Cells: Synthesis, Receptor Usage and Growth Support", J. Cell Mol. Med., vol. 13, No. 8B, pp. 2622-2633, 2009.
R. Nishiuchi et al., "Saibo Secchaku Inshi no. Seibutsugaku", Tissue Engineering, Nihon-Igakukan Co., Ltd., pp. 88-95, Jun. 27, 2007 (partial English translation).
K. Kunneken et al., "Recombinant Human Laminin-5 Domains", The Journal of Biological Chemistry, vol. 279, No. 7, pp. 5184-5193, Feb. 13, 2004.
Y. Kikkawa et al., "Integrin Binding Specificity of Laminin-10/11: Laminin-10/11 are Recognized by $\alpha 3\beta 1$, $\alpha 6 \beta 1$ and $\alpha 6\beta 4$ Integrins", Journal of Cell Science, vol. 113, pp. 869-876, 2000.
H. Ido et al., "The Requirement of the Glutamic Acid Residue at the Third Position from the Carboxyl Termini of the Laminin $\gamma$ Chains in Integrin Binding by Laminins", The Journal of Biological Chemistry, vol. 282, No. 15, pp. 11144-11154, Apr. 13, 2007.
T. Miyazaki et al., "Recombinant Human Laminin Isoforms can Support the Undifferentiated Growth of Human Embryonic Stem Cells", Biochemical and Biophysical Research Communications, vol. 375, pp. 27-32, 2008.
Y. Taniguchi et al., "The C-Terminal Region of Laminin $\beta$ Chains Modulates the Integrin Binding Affinities of Laminins", The Journal of Biological Chemistry, vol. 284, No. 12, pp. 7820-7831, Mar. 20, 2009.
A. Domogatskaya et al., "Laminin-511 but Not -332, -111, or -411 Enables Mouse Embryonic Stem Cell Self-Renewal in Vitro", Stem Cells, vol. 26, pp. 2800-2809, 2008.

\* cited by examiner

CULTURE SUBSTRATE FOR HUMAN PLURIPOTENT STEM CELLS AND USE THEREOF

TECHNICAL FIELD

The present invention relates to a culture substrate for human pluripotent stem cells and use thereof. In particular, the present invention relates to a culture substrate for human pluripotent stem cells; and a culture method of human pluripotent stem cells using the culture substrate, a method for rapid expansion of human pluripotent stem cells using the culture substrate, and a separation method of single-cell-derived clones of human pluripotent stem cells using the culture substrate.

BACKGROUND ART

Human pluripotent stem cells, such as human ES cells and human iPS cells, have attracted worldwide attention for their potential application to regenerative medicine. For culture and maintenance of human pluripotent stem cells in a pluripotent state, co-culture with feeder cells such as mouse or human fibroblasts is usually employed, but the use of feeder cells is a great restriction on clinical application of human pluripotent stem cells. In order to solve this problem, various adhesion proteins in place of feeder cells have been attempted for use as an extracellular matrix for human ES cells, and it is reported that Matrigel (trade name), which is composed of basement membrane components extracted and purified from mouse EHS sarcoma known to excessively produce basement membrane components, is highly effective in maintenance of pluripotency. However, since Matrigel is a mouse derived product and a complicated mixture of xenogeneic proteins and polysaccharides, it is not suitable for culture of human pluripotent stem cells in regenerative medicine.

For application of human pluripotent stem cells to regenerative medicine, cell culture must be performed in xeno-free conditions, in which the culture system does not contain any xenogeneic components, and in feeder-free conditions, in which feeder cells are not used. Based on these requirements, human vitronectin or human fibronectin has been attempted for use as a human extracellular matrix, but as compared with Matrigel, either of them are not superior in maintenance of undifferentiated state of human ES cells or in attachment efficiency thereof, and unsatisfactory in terms of quality, source material availability, safety, etc. Thus, in the development of extracellular matrices suitable for maintenance culture of human pluripotent stem cells, there are much to be improved, and development of a new human-pluripotent-stem-cell culture technology using a human extracellular matrix having a uniform chemical composition is strongly desired.

Laminin is a major cell-adhesion protein present in the basement membrane. Laminin is a large heterotrimeric glycoprotein consisting of three subunits termed α, β and γ chains, and has a molecular weight of 800,000 Da. The three subunits associate with each other through their coiled-coil domains in the C-terminal regions and assemble into a heterotrimer that is stabilized by disulfide bonds therein. The present inventors examined the type of integrins expressed on human ES cells, and reported that α6β1 integrin is a major adhesion receptor of human ES cells and that recombinant human laminins (particularly, laminin 332 composed of α3, β3 and γ2 chains, and laminin 511 composed of α5, β1 and γ1 chains) are effective for maintaining the pluripotency of human ES cells (see Non Patent Literature 1). The present inventors also reported that laminin 511 has a very high affinity for α6β1 integrin, and that the E8 fragment of laminin 511 has an α6β1 integrin-binding activity equivalent to that of the full-length laminin 511 (see Non Patent Literature 2).

However, since laminin binds to various cell surface molecules and extracellular matrix molecules, many technical problems must be overcome for preparation of a pure and homogeneous laminin free from impurities. In addition, since each of the three laminin subunits has a molecular weight of as large as 200,000 to 400,000 Da, the heterotrimeric molecule assembled from these subunits is not easy to be expressed as a recombinant protein, and its yield is low.

CITATION LIST

Non Patent Literature

Non Patent Literature 1:
Miyazaki T, Futaki S, Hasegawa K, Kawasaki M, Sanzen N, Hayashi M, Kawase E, Sekiguchi K, Nakatsuji N, Suemori H. Recombinant human laminin isoforms can support the undifferentiated growth of human embryonic stem cells. Biochem. Biophys. Res. Commun. 375:27-35, 2008.
Non Patent Literature 2:
Taniguchi Y, Ido H, Sanzen N, Hayashi M, Sato-Nishiuchi R, Futaki S, Sekiguchi K. The C-terminal region of laminin beta chains modulates the integrin binding affinities of laminins. J. Biol. Chem. 284:7820-7831, 2009.

SUMMARY OF INVENTION

Technical Problem

An object of the present invention is to provide a culture substrate which enables maintenance culture of human pluripotent stem cells in a pluripotent state under a feeder-free culture environment, and a culture method of human pluripotent stem cells using the culture substrate.

Solution to Problem

The present invention includes the following as a solution to the above-mentioned problems.
(1) A culture substrate for human-pluripotent-stem-cell culture, the culture substrate being coated with human laminin α5β1γ1 E8 fragment or human laminin α3β3γ2 E8 fragment.
(2) The culture substrate according to the above (1), wherein the coating concentration of human laminin α5β1γ1 E8 fragment or human laminin α3β3γ2 E8 fragment is 0.5 to 25 µg/cm².
(3) The culture substrate according to the above (1) or (2), wherein the human pluripotent stem cell is a human ES cell or a human iPS cell.
(4) A culture method of human pluripotent stem cells using the culture substrate according to any one of the above (1) to (3).
(5) A culture method of human pluripotent stem cells dissociated into single cells, comprising the steps of:
dissociating human pluripotent stem cells into single cells, and
culturing the human pluripotent stem cells dissociated into single cells using the culture substrate according to any one of the above (1) to (3).
(6) A method for rapid expansion of human pluripotent stem cells, comprising the steps of:
dissociating human pluripotent stem cells into single cells, and culturing the human pluripotent stem cells dissociated into single cells using the culture substrate according to any one of the above (1) to (3), the human pluripotent stem cells dissociated into single cells being seeded at a cell density of $2\times10^4$ to $20\times10^4$ cells/cm$^2$.

(7) A separation method of single-cell-derived clones of human pluripotent stem cells, comprising the steps of:
dissociating human pluripotent stem cells into single cells, and
culturing the human pluripotent stem cells dissociated into single cells using the culture substrate according to any one of the above (1) to (3),
the method being characterized by formation of single-cell-derived colonies.

(8) A single-cell culture method of human pluripotent stem cells, comprising the steps of:
dissociating human pluripotent stem cells into single cells, and
culturing the human pluripotent stem cells dissociated into single cells using the culture substrate according to any one of the above (1) to (3),
the method being characterized by maintenance of the human pluripotent stem cells in a single-cell state.

Advantageous Effects of Invention

According to the present invention, a culture substrate which enables maintenance culture of human pluripotent stem cells in a pluripotent state under a feeder-free culture environment, and a culture method of human pluripotent stem cells using the culture substrate are provided. In the case where a xeno-free culture medium is further used in the present invention, human pluripotent stem cells can be cultured under xeno-free and feeder-free conditions, and thus highly safe human pluripotent stem cells can be provided. Further, the culture substrate of the present invention enables rapid expansion and proliferation of human pluripotent stem cells dissociated into single cells, separation of single-cell-derived clones and maintenance of single-cell state. Furthermore, human laminin α5β1γ1 E8 fragment and human laminin α3β3γ2 E8 fragment used for coating the culture substrate can be produced as a recombinant protein in a high yield, and thus a culture substrate coated with a highly pure and homogeneous human protein can be produced in a high-quality and low-cost manner.

BRIEF DESCRIPTION OF DRAWINGS

FIG. 1 shows the comparative results of different extracellular matrices on coating concentration-dependent attachment efficiency of human ES cells.

FIG. 2 shows the results on seeding density-dependent attachment efficiency of single-cell dissociated human ES cells on the culture substrate coated with Matrigel or human laminin α5β1γ1 E8 fragment.

FIG. 3 shows human ES cell morphology on the culture substrate coated with human laminin α3β3γ2 E8 fragment.

FIG. 4 shows human ES cell morphology on the culture substrate coated with human laminin α5β1γ1 E8 fragment.

FIG. 5 shows the results of flow cytometric analysis of surface antigens on human ES cells cultured on the culture substrate coated with Matrigel, human laminin α3β3γ2 E8 fragment or human laminin α5β1γ1 E8 fragment.

DESCRIPTION OF EMBODIMENTS

Culture Substrate for Human Pluripotent Stem Cells

The present invention provides a culture substrate for human-pluripotent-stem-cell culture, the culture substrate being coated with human laminin α5β1γ1 E8 fragment or human laminin α3β3γ2 E8 fragment. Examples of the pluripotent stem cells include ES cells (embryonic stem cells), iPS cells (induced pluripotent stem cells), mGS cells (multipotent germ stem cells) and hybridomas of human ES cells and somatic cells.

The human laminin α5β1γ1 E8 fragment (hereinafter referred to as "human laminin 511E8") means a human laminin α5β1γ1 (hereinafter referred to as "human laminin 511") fragment corresponding to mouse laminin α1β1γ1 E8 fragment (hereinafter referred to as "mouse laminin 111E8"), and the human laminin α3β3γ2 E8 fragment (hereinafter referred to as "human laminin 332E8") means a human laminin α3β3γ2 (hereinafter referred to as "human laminin 332") fragment corresponding to mouse laminin 111E8.

Among fragments obtained by elastase digestion of mouse laminin α1β1γ1 (hereinafter referred to as "mouse laminin. 111"), the laminin E8 fragment was identified as a fragment that has the strongest cell adhesion activity (Edgar D., Timpl R., Thoenen H. The heparin-binding domain of laminin is responsible for its effects on neurite outgrowth and neuronal survival. EMBO J., 3:1463-1468, 1984; and Goodman S L., Deutzmann R., von der Mark K. Two distinct cell-binding domains in laminin can independently promote nonneuronal cell adhesion and spreading. J. Cell Biol., 105:589-598, 1987). Thus, it is presumed that elastase digestion of human laminin 511 and human laminin 332 could produce a fragment corresponding to mouse laminin 111E8, but there have been no reports on isolation or identification of such a fragment so far. Therefore, human laminin 511E8 and human laminin 332E8 used in the present invention do not have to be an elastase-digested product of human laminin 511 or human laminin 332, and may be any fragment of human laminin 511 or human laminin 332 as long as the fragment has a cell adhesion activity, structure and molecular weight equivalent to those of mouse laminin 111E8.

The method for producing human laminin 511E8 or human laminin 332E8 is not particularly limited. Human laminin 511E8 and human laminin 332E8 can be produced by, for example, digestion of full-length human laminin 511 or human laminin 332 with protease, such as elastase, followed by isolation and purification of the objective fragment. Alternatively, human laminin 511E8 and human laminin 332E8 can be produced as a recombinant protein. The latter is preferable in terms of production quantity, quality uniformity, production cost, etc.

Recombinant human laminin 511E8 and recombinant human laminin 332E8 can be produced by an appropriate known recombinant technique. Recombinant human laminin 511E8 can be produced by, for example, preparing DNAs encoding the α, β and γ chains of human laminin 511E8, inserting the DNAs into separate expression vectors, cointroducing the three resulting expression vectors into an appropriate host cell for expression, and purifying the objective trimeric protein by a known method. The present inventors produced recombinant human laminin 511E8 according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007) (see Examples), but the production method of recombinant human laminin 511E8 of the present invention is not limited thereto. Recombinant human laminin 332E8 can be similarly produced (see Examples). Regarding human laminin 511 subunits, namely, α5, β1 and γ1 chains, and human laminin 332 subunits, namely, α3, β3 and γ2 chains, data on the base sequence of a gene (cDNA) encoding each chain and on the amino acid sequence of each chain can be obtained from a known database (GenBank etc.) by use of each accession number shown in Table 1.

TABLE 1

Sequence data of human laminin (accession number)

| | Amino acid sequence | Base sequence |
| --- | --- | --- |
| α5 chain | NP_005551 | NM_005560 |
| β1 chain | NP_002282 | NM_002291 |
| γ1 chain | NP_002284 | NM_002293 |
| α3 chain | NP_000218 | NM_000227 |
| β2 chain | NP_000219 | NM_000228 |
| γ2 chain | NP_005553 | NM_005562 |

By diluting the prepared human laminin 511E8 or human laminin 332E8 with a suitable solvent, such as PBS, physiological saline and a physiological saline adjusted to a neutral pH with tris(hydroxymethyl)aminomethane or 4-(2-hydroxyethyl)-1-piperazine ethanesulfonic acid, adding the diluted solution to a suitable culture substrate, and leaving the culture substrate to stand at room temperature to about 37° C. for about 1 to 12 hours, the surface of the culture substrate can be coated with human laminin 511E8 or human laminin 332E8. In this way, the culture substrate of the present invention can be produced. The culture substrate to be coated is not limited as long as it can be used for culture of human pluripotent stem cells, and examples thereof include glass or plastic dishes, flasks, multiwell plates and culture slides, microcarriers and polymer membranes such as a polyvinylidene fluoride membrane.

The coating concentration of human laminin 511E8 or human laminin 332E8 is preferably about 0.5 to 25 μg/cm$^2$, and more preferably about 1.5 to 10 μg/cm$^2$. Even at such a low coating concentration, both human laminin 511E8 and human laminin 332E8 enable attachment and proliferation of a larger number of human pluripotent stem cells as compared with any of conventionally used Matrigel, human laminin 511 and human laminin 332.

The culture substrate of the present invention is coated with either or both of human laminin 511E8 and human laminin 332E8. The culture substrate may be coated with, in addition to human laminin 511E8 and/or human laminin 332E8, other human-derived components. Examples of such other human-derived components include serum components, extracellular matrix molecules, growth factors, differentiation inducing factors and morphogenetic factors (morphogens). The culture substrate may be also coated with non-biological components, such as synthetic polymer gel (synthetic polymer).

The culture substrate of the present invention, which is coated with human laminin 511E8 or human laminin 332E8, enables maintenance culture of human pluripotent stem cells in a pluripotent state under a culture environment free from feeder cells (feeder-free culture environment), which are usually used for stem cell culture. For maintenance of clonal growth and undifferentiated state, pluripotent stem cells are usually cultured in a co-culture system in which pluripotent stem cells are cultured on feeder cells, such as mouse embryonic fibroblasts (MEFs) whose proliferation has been arrested by X-ray radiation or mitomycin-C treatment. A culture system not using such feeder cells is called a feeder-free culture system.

Further, by use of a culture medium without xenogeneic components, human pluripotent stem cells can be cultured in culture conditions completely free from xenogeneic components (xeno-free culture conditions), and thus highly safe human pluripotent stem cells with an extremely low risk of developing immunogenicity for humans can be provided.

Further, the culture substrate of the present invention enables culture of human pluripotent stem cells dissociated into single cells, which has been infeasible in conventional culture systems. Therefore, human pluripotent stem cells can be expanded and proliferated significantly more rapidly as compared with in conventional culture systems. Further, single-cell-derived clones of human pluripotent stem cells can be separated easily and maintained in a single-cell state.

<Culture Method of Human Pluripotent Stem Cells>

The present invention provides a culture method of human pluripotent stem cells using the above-mentioned culture substrate of the present invention. The culture method of the present invention is preferably used in the case of human pluripotent stem cell culture in feeder-free culture conditions, and particularly preferably used in the case of human pluripotent stem cell culture in feeder-free and xeno-free culture conditions.

The culture medium used in the culture method of the present invention is not particularly limited, but a synthetic medium is preferable and a synthetic medium without xenogeneic components (xeno-free synthetic medium) is particularly preferable. Examples of the synthetic medium which is or will be commercially available include mTeSR1 (trade name, StemCell Technologies), TeSR2 (trade name, StemCell Technologies), StemPro hESC SFM (trade name, Invitrogen) and hESF-GRO (trade name, Cell Science & Technology Institute, Inc.). Among these, TeSR2 is a culture medium without xenogeneic components. Also, the culture media described in the following References (1) to (5) can be preferably used.

(1) Liu, Y. et al., Biochem. Biophys. Res. Commun., 346:131-139, 2006.
(2) Vallier, L. at al., J. Cell Sci. 118:4495-4509, 2005.
(3) Li, Y. et al., Biotechnol. Bioeng., 91:688-698, 2005.
(4) Yao, S. et al., Proc. Natl. Acad. Sal. U.S.A., 103:6907-6912, 2006.
(5) Lu, J. et al., Proc. Natl. Acad. Sci. U.S.A., 103:5688-5693, 2006.

A embodiment in the case of culturing human ES cells according to the culture method of the present invention is shown below. The culture method of the present invention is not limited as long as human pluripotent stem cells are cultured by use of the above-mentioned culture substrate of the present invention, and is not limited to this embodiment, either.

(1) Collection of Human ES Cells from Feeder Cell Co-Culture System

Human ES cells are collected from a feeder cell co-culture system according to the following method 1 or 2.

Method 1:

To a culture dish in which human ES cells have been co-cultured with feeder cells (for example, MEFs) (Day 3 to Day 5), 0.25% trypsin/DMEM-F12 (for example, 1 ml/60 mm dish) is added, and trypsin treatment is performed at 37° C. for 2 to 3 minutes. The culture dish is washed with DMEM-F12 and thereby feeder cells are removed. Then, a culture medium is added to the culture dish and the entire cells on the culture dish are physically detached. The resulting cell suspension is filtered through a BD Falcon 100-μm cell strainer (BD Falcon #352460), the strainer is washed, and thus only human ES cell colonies are separated and collected.

Method 2:

To a culture dish in which human ES cells have been co-cultured with feeder cells (for example, MEFs) (Day 3 to Day 5), a human-ES-cell detachment solution (for example, Dissociation Solution for Primate ES Cells (RCHETP002 manufactured by ReproCELL Inc.), 1 mg/ml Dispase/DMEM-F12, 10 mg/ml collagenase IV/DMEM-F12, etc.) (for example, 1 ml/60 mm dish) is added, and detachment treatment is performed at 37° C. for 5 minutes. As a result, the human ES cells and MEFs are detached from the culture dish. Then, the detached cells are transferred into a 15-ml centrifuge tube. To this tube, about 10 ml of a culture medium is added, the cells are suspended, the tube is left to stand for 5 minutes to allow only the colonies to precipitate, and then the supernatant is removed. By repeating this procedure twice or more, only human ES cell colonies are collected.

(2) Transfer of Human ES Cells onto Culture Substrate of Present Invention

The collected human ES cell colonies are dissociated into single cells. The method for dissociating the colonies into single cells is not particularly limited, and for example, the colonies can be dissociated by flushing with a culture medium several times using a Pipetman P-1000 or the like. The cells dissociated into single cells are resuspended in an appropriate culture medium (for example, TeSR2 etc.), and seeded onto a culture substrate of the present invention (for example, a culture dish coated with human laminin 511E8 (1.5 μg/cm$^2$)). Culture is performed in a $CO_2$ concentration condition suitable for the culture medium used, and the culture medium is changed daily.

(3) Passage Culture

Passage is performed at the time when shortage of space for further expansion or dead cells in the colonies become visible. In the culture method of the present invention, passage may be performed by seeding human ES cells maintained as moderate-sized colonies, as in conventional methods. Alternatively, passage may be performed by seeding human ES cells dissociated into single cells. Here, the state of "dissociated into single cells" does not only mean a state in which all the cells in a cell suspension are present as a single cell, but includes a state in which some cells in a cell suspension are present as a single cell and other cells therein are present in an aggregate form of about several to a little more than ten cells.

In the Case of Cells Dissociated into Single Cells:

To a culture substrate of the present invention (for example, a culture dish coated with human laminin 511E8 (1.5 μg/cm$^2$)) on which human ES cells have been cultured, TrypLE Select (trade name, Invitrogen #12563011) (for example, 1 ml/60 mm dish) is added, and the human ES cells are treated therewith at 37° C. for 5 minutes. The human ES cell colonies are dissociated into single cells by, for example, flushing with a culture medium several times using a Pipetman P-1000 or the like. After addition of a culture medium, the human ES cells are suspended and then collected in a centrifuge tube. After a step of centrifugation (200×g, 3 minutes) and a subsequent step of washing with a culture medium are repeated twice, the human ES cells are resuspended in a fresh culture medium and seeded in a single-cell state at a cell density of, for example, about 40,000 cells/cm$^2$ onto a culture substrate of the present invention (for example, a culture dish coated with human laminin 511E8 (1.5 μg/cm$^2$)). Culture is performed in a $CO_2$ concentration condition suitable for the culture medium used, and the culture medium is changed daily.

In the Case of Cells not Dissociated into Single Cells:

In this case, enzymes, such as collagenase IV, Dispase and Accutase, are used for cell detachment. To a culture substrate of the present invention on which human ES cells have been cultured, 10 mg/ml collagenase/DMEM-F12, 2 mg/ml Dispase/DMEM-F12 or Accutase (Millipore #SCR005) (for example, 1 ml/60 mm dish) is added, and the human ES cells are treated therewith at 37° C. for 5 minutes. After removal of the enzyme solution, a culture medium is added, and the human ES cell colonies are split into smaller-sized colonies composed of about 50 to 100 cells by, for example, flushing with a culture medium several times using a Pipetman P-1000 or the like. The cell suspension is collected in a centrifuge tube. After a step of centrifugation (200×g, 3 minutes) and a subsequent step of washing with a culture medium are repeated twice, the human ES cells are resuspended in a fresh culture medium and seeded in a 2- to 4-fold dilution onto a culture substrate of the present invention (for example, a culture dish coated with human laminin 511E8 (1.5 μg/cm$^2$)). Culture is performed in a $CO_2$ concentration condition suitable for the culture medium used, and the culture medium is changed daily.

<Method for Rapid Expansion of Human Pluripotent Stem Cells>

The present invention provides a method for rapid expansion of human pluripotent stem cells. The rapid expansion method of the present invention comprises the steps of: dissociating human pluripotent stem cells into single cells, and culturing the human pluripotent stem cells dissociated into single cells using the above-mentioned culture substrate of the present invention, the human pluripotent stem cells dissociated into single cells being seeded at a cell density of about $2 \times 10^4$ to $20 \times 10^4$ cells/cm$^2$. The seeding density is more preferably about $3 \times 10^4$ to $10 \times 10^4$ cells/cm$^2$, and still more preferably about $4 \times 10^4$ to $5 \times 10^4$ cells/cm$^2$. At such a seeding density, the attachment efficiency of human ES cells dissociated into single cells in conventional culture systems is less than 10%, but the rapid expansion method of the present invention can achieve a significantly higher attachment efficiency, and enables subsequent vigorous proliferation, therefore allowing human pluripotent stem cells to proliferate at a remarkably higher speed than that in conventional methods.

In the step of dissociating human pluripotent stem cells into single cells, as in the above-mentioned "In the case of cells dissociated into single cells," human pluripotent stem cell colonies are detached and collected from a culture dish, and these colonies are dissociated into single cells by, for example, flushing with a culture medium several times using a Pipetman P-1000 or the like. Then, the cell number is counted by a known cell counting method, and the cell concentration of the cell suspension is appropriately adjusted to provide the above-mentioned seeding density. The culturing step can be performed according to the description in the above culture method of the present invention.

<Separation Method of Single-Cell-Derived Clones of Human Pluripotent Stem Cells>

The present invention provides a separation method of single-cell-derived clones of human pluripotent stem cells. The separation method of the present invention comprises the steps of: dissociating human pluripotent stem cells into single cells, and culturing the human pluripotent stem cells dissociated into single cells using the above-mentioned culture substrate of the present invention, and the method is characterized by formation of single-cell-derived colonies. According to the separation method of the present invention, unlike in conventional culture systems, single-cell-derived clones of human pluripotent stem cells can be easily formed and separated, and thus homogeneous human pluripotent stem cells can be easily obtained.

For formation of single-cell-derived colonies and separation of single-cell-derived clones, any method may be used without particular limitation, and for example, a known limiting dilution etc. can be preferably used. Depending on the method used, the cell density and the culture substrate of the present invention to be used are appropriately selected, and under the selected conditions, human pluripotent stem cells dissociated into single cells are seeded and cultured. The culturing step can be performed according to the description in the above culture method of the present invention.

<Single-Cell Culture Method of Human Pluripotent Stem Cells>

The present invention provides a single-cell culture method of human pluripotent stem cells. The single-cell culture method of the present invention comprises the steps of: dissociating human pluripotent stem cells into single cells, and culturing the human pluripotent stem cells dissociated into single cells using the above-mentioned culture substrate of the present invention, and the method is characterized by maintenance of the human pluripotent stem cells in a single-cell state without proliferation. Generally, in the colony formed of human pluripotent stem cells, the cells in the edge of the colony may be different in cell condition from those inside the colony, but according to the single-cell culture method of the present invention, human pluripotent stem cells do not form colonies and thus can be obtained in a uniform condition, and enhancement in efficiency of differentiation induction can be expected.

For maintenance of the human pluripotent stem cells in a single-cell state without proliferation, it is preferable that the human pluripotent stem cells dissociated into single cells are seeded at an appropriate cell density selected depending on the culture substrate of the present invention to be used, and then used for other applications before the cells proliferate. Also, it is possible that, for example, a culture medium with no or less growth factor is used for prolonged maintenance of the cells in a single-cell state.

EXAMPLES

Hereinafter, the present invention will be illustrated in detail by Examples, but is not limited thereto.

<Materials for Experiments>

(1) Extracellular Matrices

Recombinant human laminin 511E8 (hereinafter referred to as "rhLM511E8"), recombinant human laminin 332E8 (hereinafter referred to as "rhLM332E8"), recombinant human laminin 511 (hereinafter referred to as "rhLM511"), recombinant human laminin 332 (hereinafter referred to as "rhLM332"), recombinant human laminin 111 (hereinafter referred to as "rhLM111"), Matrigel (BD Bioscience #354230), human fibronectin (purified using a gelatin affinity column according to the method of Sekiguchi et al. (Sekiguchi K. and Hakomori S.: Domain structure of human plasma fibronectin. Differences and similarities between human and hamster fibronectins. The Journal of Biological Chemistry, 258, 3967-3973, 2003)) and vitronectin (purified using a heparin affinity column according to the method of Yatohgo et al. (Yatohgo T., Izumi, M., Kashiwagi, H., and Hayashi, M. Novel purification of vitronectin from human plasma by heparin affinity chromatography. Cell Structure and Function, 13, 281-292, 1988)) were used.

(2) Cells Used for Experiments

As a human ES cell, strains established in Institute for Frontier Medical Sciences, Kyoto University (KhES-1, KhES-2, KhES-3) and strains purchased from National Stem Cell Bank (H1, H9) were used. As a human iPS cell, strains purchased from National Stem Cell Bank (clone name: iPS (IMR90)-1-DL-1, iPS(IMR90)-4-MCB-1, iPS(foreskin)-1-DL-1) were used.

Maintenance culture of these cells was performed according to the respective culture methods which the organizations recommend. For example, human ES cells H9 were maintained by co-culture with mouse feeder cells according to a method recommended by National Stem Cell Bank. After 0.25% trypsin/DMEM-F12 was added to the co-culture dish and mouse feeder cells were removed, the cell suspension was filtered through a BD Falcon 100-μm cell strainer (BD Falcon #352460), the strainer was washed, and thus human ES cells H9 colonies were separated. The colonies in the strainer were collected in a human-ES-cell culture medium and split into smaller colonies by use of a Pipetman P-1000. Then, the smaller colonies were resuspended in mTeSR1 (StemCell Technologies) and seeded onto a Matrigel-coated culture substrate. The passage number of the freshly-seeded cells was designated as P1. Expansion culture was performed in a 5% $CO_2$/95% air atmosphere and continued until Day 4. During the expansion culture, the medium was replaced daily with checking for contamination with mouse feeder cells. Cells confirmed as not contaminated with mouse feeder cells were used in the experiments. Maintenance culture and expansion culture of the other kinds of cells were similarly performed, and then these cells were used in experiments. In the following Examples, only the results of human ES cells H9 are shown, but the similar results were obtained in respect of the other kinds of cells.

(3) Preparation Method of rhLM511E8 rhLM511E8 was prepared in the following manner according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

First, by PCR using a cloning plasmid pBluescript KS(+) (Stratagene) as a template, three kinds of pBluescript KS(+) containing a DNA encoding a 6×His tag (HHHHHH), a DNA encoding an HA (hemagglutinin) tag (YPYDVPDYA) or a DNA encoding a FLAG tag (DYKDDDDK) inserted at the 5' end of the EcoRV site in the multicloning site were prepared. The pairs of primers used for the PCR are as follows.

(i) Primers for 6×His Tag Insertion

```
                                   (forward, SEQ ID NO: 1)
       5'-ATGATGATGAAGCTTATCGATACCGT-3'

(reverse, SEQ ID NO: 2)
       5'-CATCATCATGATATCGAATTCCTGCA-3'
```

(ii) Primers for HA Tag Insertion

```
                                   (forward, SEQ ID NO: 3)
       5'-ATCATATGGATAAAGCTTATCGATACCGT-3'

(reverse, SEQ ID NO: 4)
       5'-GTGCCAGATTATGCAGATATCGAATTCCT-3'
```

(iii) Primers for FLAG Tag Insertion

```
                                   (forward, SEQ ID NO: 5)
       5'-ATCCTTGTAATCAAGCTTATCGATACCGT-3'

(reverse, SEQ ID NO: 4)
       5'-GTGCCAGATTATGCAGATATCGAATTCCT-3'
```

Next, by PCR using plasmids containing the full-length base sequences of α5, β1 and γ1 chains (Ido et al., J. Biol. Chem., 279, 10946-10954, 2004) as templates, the regions corresponding to α5 (Ala$^{2534}$-Ala$^{3327}$) β1 (Leu$^{1561}$-Leu$^{1786}$) and γ1 (Asn$^{1362}$-Pro$^{1608}$) were amplified, respectively. The primers used for the PCR are as follows.

(iv) Primers for Amplification of α5 Chain E8 Fragment

```
                                    (forward, SEQ ID NO: 6)
5'-GCTGCCGAGGATGCTGCTGGCCAGG-3'

(reverse, SEQ ID NO: 7)
5'-CTAGGCAGGATGCCGGGCGGGCTGA-3'
```

(v) Primers for Amplification of β1 Chain E8 Fragment

```
                                    (forward, SEQ ID NO: 8)
5'-CTTCAGCATAGTGCTGCTGACATTG-3'

(reverse, SEQ ID NO: 9)
5'-TTACAAGCATGTGCTATACACAGCAAC-3'
```

(vi) Primers for Amplification of γ1 chain E8 Fragment

```
                                    (forward, SEQ ID NO: 10)
5'-AATGACATTCTCAACAACCTGAAAG-3'

(reverse, SEQ ID NO: 11)
5'-CTAGGGCTTTTCAATGGACGGGGTG-3'
```

The amplified cDNAs were separately inserted into the EcoRV site in the multicloning site of the above-prepared pBluescript KS(+) containing a tag sequence. Then, the region containing the amplified cDNA and the 5'-terminal tag-encoding sequence was digested with restriction enzymes EcoRI and HindIII, and inserted into the corresponding restriction site of pSecTag2B, an expression vector designed for mammalian cells (Invitrogen). In this way, expression vectors for human α5 chain E8 fragment (containing the 6×His tag in the N-terminal region), human 131 chain E8 fragment (containing the HA tag in the N-terminal region), and human γ1 chain E8 fragment (containing the FLAG tag in the N-terminal region) were prepared.

For expression of rhLM511E8, the three expression vectors were introduced into human embryonic kidney-derived cells 293F (purchased from Invitrogen). 180 μg each of these expression vectors were co-transfected into 300 ml of 293F cells (1.0×10$^6$ cells/ml) by use of a transfection reagent 293fectin (trade name, Invitrogen) and Opti-MEM (trade name, Invitrogen), and the cells were cultured for 72 hours. After this, the culture medium was collected. The collected culture medium was centrifuged at 1,000×g for 10 minutes, and the resulting supernatant was further centrifuged at 15,000×g for 30 minutes for removal of insoluble matter and remaining cells. To the resulting supernatant, 5 ml of Ni-NTA agarose (QIAGEN) was added and the objective protein was allowed to bind thereto by overnight incubation. The Ni-NTA agarose was collected and washed successively with TBS(−) (tris-buffered saline without Ca or Mg) and 10 mM imidazole/TBS(−), and bound proteins were eluted with 200 mM imidazole/TBS(−). The rhLM511E8 thus eluted was confirmed by SDS-PAGE followed by silver staining. To the rhLM511E8-containing fraction, 2 ml of ANTI-FLAG M2 affinity Gel (Sigma) was added and the mixture was rotated at 4° C. overnight. The affinity gel was transferred into an Econo Column, which was then washed with TBS (−) containing 1 mM PMSF. Then, elution was performed with TBS(−) containing 100 μg/ml FLAG peptide (Sigma). After the eluted fractions were subjected to silver staining, rhLM511E8-containing fractions were combined and dialyzed against TBS (−).

(4) Preparation Method of rhLM332E8

(4-1) Preparation of Expression Vector for Human Laminin α3 Chain E8 Fragment

First, by PCR using a cloning plasmid pBluescript KS(+) (Stratagene) as a template, a pBluescript KS(+) containing the restriction enzyme AscI recognition sequence (GGCGCGCC) and a DNA encoding a 6×His tag (HHH-HHH) inserted at the 5' end of the EcoRV site in the multicloning site was prepared. The pair of primers used for the PCR is as follows.

(vii) Primers for 6×His Tag Insertion

```
                                    (forward, SEQ ID NO: 12)
5'-ATGATGATGGGCGCGCCAAGCTTATCGATACCGT-3'

(reverse, SEQ ID NO: 13)
5'-CATCATCATGATATCGAATTCCTGC-3'
```

Next, by PCR using a plasmid containing the cDNA sequence of human laminin α3 chain (lacking the 4th and 5th laminin globular domains) (Ido et al., J. Biol. Chem., 282, 11144-11154, 2007) as a template, the region corresponding to α3 (Ala$^{579}$-Ala$^{1364}$) was amplified. The primers used for the PCR are as below. The reverse primer contains the XbaI recognition sequence (TCTAGA) in the 5'-terminal region.

(viii) Primers for Amplification of α3 Chain E8 Fragment

```
                                    (forward, SEQ ID NO: 14)
5'-GCGGCCGAGGACGCAGCCAACAGG-3'

(reverse, SEQ ID NO: 15)
5'-GGTCTAGACTAAGCATCTTGCCACACC-3'
```

The amplified cDNA was inserted into the EcoRV-XbaI site in the multicloning site of the above-prepared pBluescript KS(−) containing the AscI recognition sequence and the 6×His tag-encoding sequence. Then, the cDNA containing the α3 chain E8 fragment-encoding sequence and the 5'-terminal 6×His tag-encoding sequence was digested with restriction enzymes AscI and NotI, and inserted into the corresponding restriction site of pSecTag2A, an expression vector designed for mammalian cells (Invitrogen). In this way, an expression vector for human α3 chain E8 fragment (containing the 6×His tag in the N-terminal region) was prepared.

(4-2) Preparation of Expression Vector for Human Laminin β3 Chain E8 Fragment

For preparation of a cDNA fragment encoding a mouse Ig-κ chain V-J2-C signal peptide, an HA tag and β3 chain E8 fragment in this order from the 5' end, a cDNA fragment encoding a mouse Ig-κ chain V-J2-C signal peptide and an HA tag, and a cDNA fragment encoding β3 chain E8 were separately obtained, and these two fragments were ligated and amplified by extension PCR.

First, by PCR using a human laminin β1 chain E8 expression vector (Ido et al., J. Biol. Chem., 282, 11144-11154, 2007) as a template, the region corresponding to a mouse Ig-κ chain V-J2-C signal peptide and an HA tag was amplified. The primers used for the PCR are as below. The reverse primer contains a sequence used for extension PCR in the 5'-terminal region.

(ix) Primers for Amplification of Signal Peptide Sequence and HA Tag Sequence

```
                                 (forward, SEQ ID NO: 16)
5'-TGGGCGTGGATAGCGGTTTG-3'

(reverse, SEQ ID NO: 17)
5'-TCTGGGACAGATCTGCATAATCTGGCAC-3'
```

Next, by PCR using a plasmid containing the cDNA sequence of human laminin β3 chain (Ido et al., J. Biol. Chem., 282, 11144-11154, 2007) as a template, the region corresponding to β3 (Leu$^{949}$-Lys$^{1172}$) was amplified. The primers used for the PCR are as below. The forward primer contains a sequence used for extension PCR in the 5'-terminal region, and the reverse primer contains the EcoRI recognition sequence (GAATTC) in the 5'-terminal region.

(x) Primers for Amplification of β3 Chain E8 Fragment

```
                                 (forward, SEQ ID NO: 18)
5'-AGATTATGCAGATCTGTCCCAGACCAAG-3'

(reverse, SEQ ID NO: 19)
5'-GCGAATTCTCACTTGCAGGTGGCATA-3'
```

The two kinds of resulting cDNA fragments were ligated and amplified by extension PCR using the primers described below, to give a cDNA fragment encoding a mouse Ig-κ chain V-J2-C signal peptide, an HA tag and β3 chain E8. Then, the amplified cDNA was digested with restriction enzymes NheI and EcoRI, and inserted into the corresponding restriction site of pSecTag2B, an expression vector designed for mammalian cells (Invitrogen). In this way, an expression vector for human β3 chain E8 fragment (containing the HA tag in the N-terminal region) was prepared. The NheI recognition sequence (GCTAGC) is located at the immediate 5' end of the initiation codon.

(xi) Primers for Amplification of Mouse Ig-κ Chain V-J2-C Signal Peptide, HA Tag and β3 Chain E8

```
                                 (forward, SEQ ID NO: 16)
5'-TGGGCGTGGATAGCGGTTTG-3'

(reverse, SEQ ID NO: 19)
5'-GCGAATTCTCACTTGCAGGTGGCATA-3'
```

(4-3) Preparation of Expression Vector for Human Laminin γ2 Chain E8 Fragment

For preparation of a cDNA fragment encoding a mouse Ig-κ chain V-J2-C signal peptide, a FLAG tag and γ2 chain ES fragment in this order from the 5' end, a cDNA fragment encoding a mouse Ig-κ chain V-J2-C signal peptide and a FLAG tag, and a cDNA fragment encoding γ2 chain E8 were separately obtained, and these two fragments were ligated and amplified by extension PCR.

First, by PCR using a human laminin γ1 chain E8 expression vector (Ido et al., J. Biol. Chem., 282, 11144-11154, 2007) as a template, the region corresponding to a mouse Ig-κ chain V-J2-C signal peptide and a FLAG tag was amplified. The primers used for the PCR are as below. The reverse primer contains a sequence used for extension PCR in the 5'-terminal region.

(xii) Primers for Amplification of Signal Peptide Sequence and FLAG Tag Sequence

```
                                 (forward, SEQ ID NO: 16)
5'-TGGGCGTGGATAGCGGTTTG-3'

(reverse, SEQ ID NO: 20)
5'-GGATGCTCTCATCCTTATCATCATCATCC-3'
```

Next, by PCR using a plasmid containing the cDNA sequence of human laminin γ2 chain (Ido et al., J. Biol. Chem., 282, 11144-11154, 2007) as a template, the region corresponding to γ2 (Glu$^{949}$-Gln$^{1172}$) was amplified. The primers used for the PCR are as below. The forward primer contains a sequence used for extension PCR in the 5'-terminal region, and the reverse primer contains the EcoRI recognition sequence (GAATTC) in the 5'-terminal region.

(xiii) Primers for Amplification of γ2 Chain E8 Fragment

```
                                 (forward, SEQ ID NO: 21)
5'-GATGATGATAAGGATGAGAGCATCCTTAAAAAC-3'

(reverse, SEQ ID NO: 22)
5'-GCGAATTCTCACTGTTGCTCAAGAGCCTG-3'
```

The two kinds of resulting cDNA fragments were ligated and amplified by extension PCR using the primers described below, to give a cDNA fragment encoding a mouse Ig-κ chain V-J2-C signal peptide, a FLAG tag and γ2 chain E8. Then, the amplified cDNA was digested with restriction enzymes NheI and EcoRI, and inserted into the corresponding restriction site of pSecTag2B, an expression vector designed for mammalian cells (Invitrogen). In this way, an expression vector for human γ2 chain E8 fragment (containing the FLAG tag in the N-terminal region) was prepared.

(xiv) Primers for Amplification of Mouse Ig-κ Chain V-J2-C Signal Peptide, FLAG Tag and γ2 Chain E8

```
                                 (forward, SEQ ID NO: 16)
5'-TGGGCGTGGATAGCGGTTTG-3'

(reverse, SEQ ID NO: 22)
5'-GCGAATTCTCACTGTTGCTCAAGAGCCTG-3'
```

(4-4) Expression and Purification of rhLM332E8

For expression of rhLM332E8, the three expression vectors were introduced into human embryonic kidney-derived cells 293F (Invitrogen). 70 μg each of these expression vectors were co-transfected into 300 ml of 293F cells ($1.0 \times 10^6$ cells/ml) by use of a transfection reagent 293fectin (trade name, Invitrogen) and Opti-MEM (trade name, Invitrogen), and the cells were cultured for 72 hours. After this, the culture medium was collected. The collected culture medium was centrifuged at 1,000×g for 10 minutes, and the resulting supernatant was further centrifuged at 15,000×g for 30 minutes for removal of insoluble matter and remaining cells. Imidazole was added to the resulting supernatant so that the final concentration might be 10 mM, and the mixture was stirred well. To this, 40 ml of 50% (v/v) Ni-NTA agarose (QIAGEN) was added and the objective protein was allowed to bind thereto in a batch method at 4° C. overnight. The Ni-NTA agarose was collected and washed with TBS(−), and elution was performed with 200 mM imidazole/TBS(−). The rhLM332E8-containing fraction was identified based on the absorbance at 280 nm. To the objective eluted fraction, 2 ml of ANTI-FLAG M2 affinity Gel (Sigma) was added and the objective protein was allowed to bind thereto in a batch method at 4° C. overnight. The affinity gel was transferred into an Econo Column (manufactured by Bio-Rad Laboratories, Inc.), which was then washed with TBS(−). Then, elution was performed with TBS(−) containing 100 μg/ml FLAG peptide (Sigma). After the eluted fractions were subjected to silver staining, the rhLM332E8-containing fraction was dialyzed (20 kDa cut) against TBS(−).

(5) Preparation Methods of Recombinant Human Laminins (rhLM511, rhLM332, rhLM111)

rhLM511 was prepared according to the method of Ido et al. (Hiroyuki Ido, Kenji Harada, Sugiko Futaki, Yoshitaka Hayashi, Ryoko Nishiuchi, Yuko Natsuka, Shaoliang Li, Yoshinao Wada, Ariana C. Combs, James M. Ervasti, and Kiyotoshi Sekiguchi, "Molecular dissection of the α-dystroglycan- and integrin-binding sites within the globular domain of human laminin-10" The Journal of Biological Chemistry, 279, 10946-10954, 2004).

rhLM332 was prepared according to the method of Ido et al. (Hiroyuki Ido, Aya Nakamura, Reiko Kobayashi, Shunsuke Ito, Shaoliang Li, Sugiko Futaki, and Kiyotoshi Sekiguchi, "The requirement of the glutamic acid residue at the third position from the carboxyl termini of the laminin γ chains in integrin binding by laminins" The Journal of Biological Chemistry, 282, 11144-11154, 2007).

rhLM111 was prepared according to the method of Ido et al. (Hiroyuki Ido, Kenji Harada, Yoshiki Yagi, and Kiyotoshi Sekiguchi, "Probing the integrin-binding site within the globular domain of laminin-511 with the function-blocking monoclonal antibody 4C7" Matrix Biology, 25, 112-117, 2006) and the method of Taniguchi et al. (Yukimasa Taniguchi, Hiroyuki Ido, Noriko Sanzen, Maria Hayashi, Ryoko Sato-Nishiuchi, Sugiko Futaki, and Kiyotoshi Sekiguchi, "The C-terminal region of laminin β chains modulates the integrin binding affinities of laminins" The Journal of Biological Chemistry, 284, 7820-7831, 2009).

Example 1

Comparison of Different Extracellular Matrices Based on Coating Concentration-Dependent Attachment Efficiency of Human ES Cells rhLM511E8, rhLM332E8, rhLM511, rhLM332, rhLM111, Matrigel, fibronectin and vitronectin were separately diluted with Dulbecco's PBS (Wako Pure Chemical Industries, Ltd. #045-29795) or DMEM-F12 (Sigma #D6241), and then added to separate 96-well microtiter plates (BD Bioscience #351172) at the final concentrations ranging 0 to 25 μg/cm$^2$. The plates were left to stand at room temperature for 2 hours and thus coated with the above extracellular matrices.

The human ES cells cultured with mTeSR1 (P1) were treated with TrypLE Select (Invitrogen #12563011) at 37° C. for 3 minutes and thereby dissociated into single cells. After the cell number was counted, the cells were seeded at a cell density of 5×10$^4$ cells/well on the plates. At 6 hours after seeding, the supernatants were removed, the wells were washed once with DMEM-F12, and the cells were fixed with 10% neutral buffered formalin for 10 minutes. The neutral buffered formalin was replaced by 100% ethanol, and 5 minutes later, the cells were stained with a 4% crystal violet/100% methanol solution for 5 minutes. The plates were dipped in a large amount of distilled water for removal of an excess stain solution and then air-dried. The cells were lysed with 1% SDS and the absorbance at a wavelength of 570 nm was measured with a multiplate reader.

Figure 1:
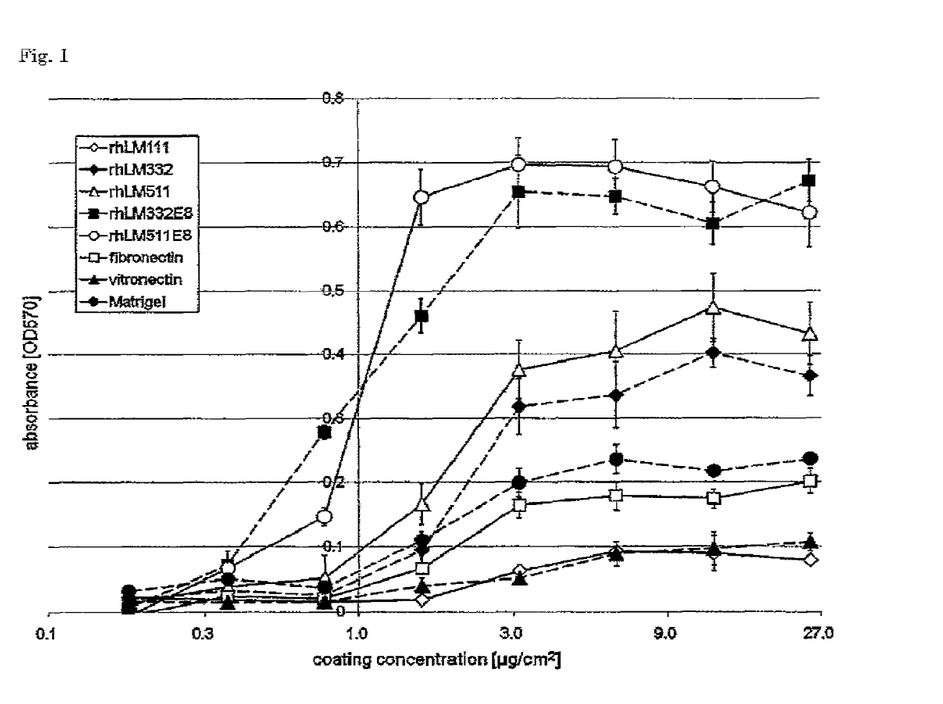

The results are shown in FIG. 1. As is clear from FIG. 1, the number of human ES cells attached onto the plates coated with rhLM511E8 or rhLM332E8 was significantly larger even at low coating concentrations. The number of human ES cells attached onto the plates coated with rhLM511E8 was larger at each coating concentration than the number of human ES cells attached onto the plates coated with Matrigel, which had been considered to be the most effective for the attachment of human ES cells among known extracellular matrix proteins. Onto the plates coated with rhLM511E8 or rhLM332E8, a larger number of human ES cells attached even at a lower coating concentration than that of the corresponding full-length laminin (rhLM511 and rhLM332). These results demonstrate that the optimum coating concentrations of rhLM511E8 and rhLM332E8 are about 1.0 to 20 μg/cm$^2$.

Example 2

Effects of Seeding Density on the Attachment Efficiency of Single-Cell Dissociated Human ES Cells on Culture Substrate Coated with rHLM511E8

In the passage of human ES cells, since dissociating the cells into single cells with trypsin/EDTA etc. causes a marked decline in viability, the cells are usually passaged in the form of a colony. In this example, the attachment efficiency of single-cell dissociated human ES cells onto a rhLM511E8-coated culture substrate was compared with that of single-cell dissociated human ES cells onto a Matrigel-coated culture substrate.

rhLM511E8 was diluted with Dulbecco's PBS so that the final concentration might be 1.5 μg/cm$^2$. Matrigel was diluted with DMEM-F12 so that the final concentration might be 25 μg/cm$^2$. The two diluted solutions were added to separate 48-well multiwell plates (BD Bioscience #351178), and the plates were left to stand at room temperature for 2 hours and thus coated with rhLM511E8 or Matrigel.

The human ES cells cultured with mTeSR1 (P1) were treated with TrypLE Select at 37° C. for 3 minutes and thereby dissociated into single cells. The cells were seeded at cell densities ranging 1×10$^3$ to 5×10$^5$ cells/cm$^2$ in triplicate wells of the 48-well multiwell plate coated with rhLM511E8 or Matrigel. At 6 hours after seeding, the supernatants were removed, the wells were washed with PBS, and the cells were detached with 0.25% trypsin/EDTA. The cell number was counted, and the ratio of the number of attached cells relative to that of seeded cells at each cell density was determined.

Figure 2:
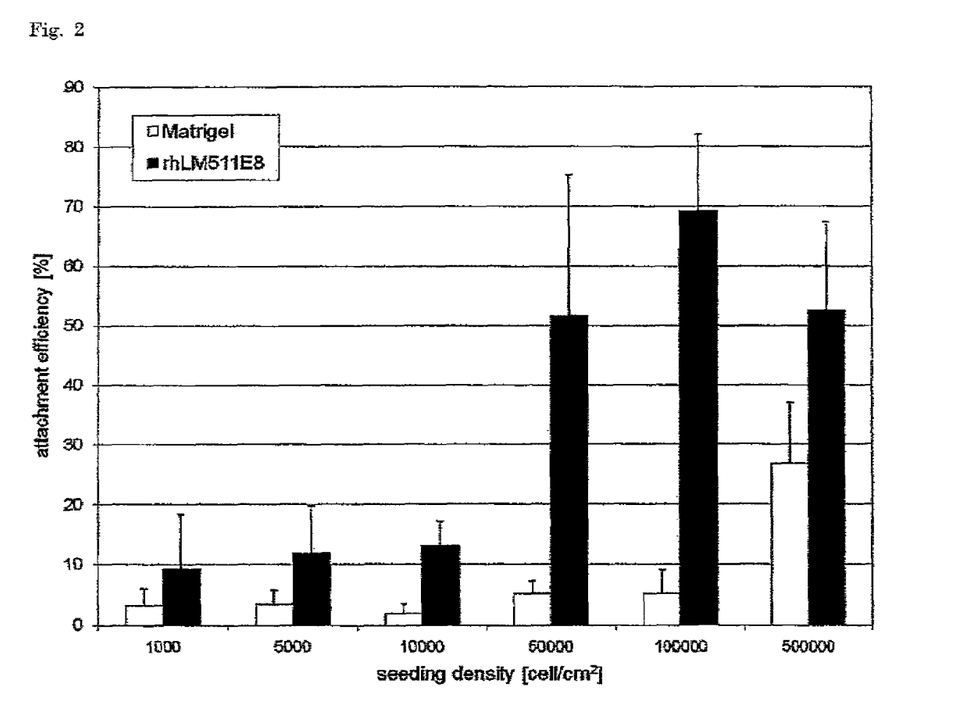

The results are shown in FIG. 2. As is clear from FIG. 2, the attachment efficiency of single-cell dissociated human ES cells seeded onto the Matrigel-coated plate was extremely low as usual, while the attachment efficiency as well as the viability of single-cell dissociated human ES cells seeded onto the rhLM511E8-coated plate were as high as about 50% at a seeding density of 5×10$^4$ cells/cm$^2$. These results demonstrate that the appropriate seeding density on a culture substrate coated with rhLM511E8 is about 5×10$^4$ to 10×10$^4$ cells/cm$^2$.

Example 3

Morphological Observation and Surface Antigen Analysis of Human ES Cells on Culture Substrate Coated with rhLM511E8 or rhLM332E8 rhLM511E8 and rhLM332E8 were separately diluted with Dulbecco's PBS so that the final concentration might be 1.5 μg/cm$^2$. Matrigel was diluted with DMEM-F12 so that the final concentration might be 25 μg/cm$^2$. The three diluted solutions were added to separate 35-mm Easy-Grip Cell Culture Dishes (BD Falcon #353001), and the dishes were left to stand at room temperature for 2 hours and thus coated with rhLM511E8, rhLM332E8 or Matrigel.

The human ES cells cultured with mTeSR1 (P1) were treated with TrypLE Select at 37° C. for 3 minutes and thereby dissociated into single cells. The cells were seeded at a cell density of $5 \times 10^4$ cells/cm$^2$ on the 35-mm Easy-Grip Cell Culture Dishes coated with rhLM511E8, rhLM332E8 or Matrigel. After seeding, the cells were photographically recorded on a daily basis.

For surface antigen analysis, at 5 days after seeding, the cells were dissociated into single cells by 3-minute treatment with TrypLE Select, and washed with Working Solution (0.1% BSA/PBS). Anti-SSEA-1 antibody, anti-SSEA-4 antibody, anti-Tra-1-60 antibody, anti-Tra-1-81 antibody, anti-Tra-2-54 antibody (all the above, Developmental Studies Hybridoma Bank, The University of Iowa) or anti-GCTM-2 antibody (Invitrogen) was added as a primary antibody and the cells were stained therewith at 4° C. for 30 minutes. Then, the cells were washed with Working Solution. Next, the cells were stained with a secondary antibody (Beckman Coulter #731735) at 4° C. for 30 minutes. Then, the cells were washed twice with Working Solution and the fluorescence intensity was measured with BD FACS Calibur HG.

Figure 3:
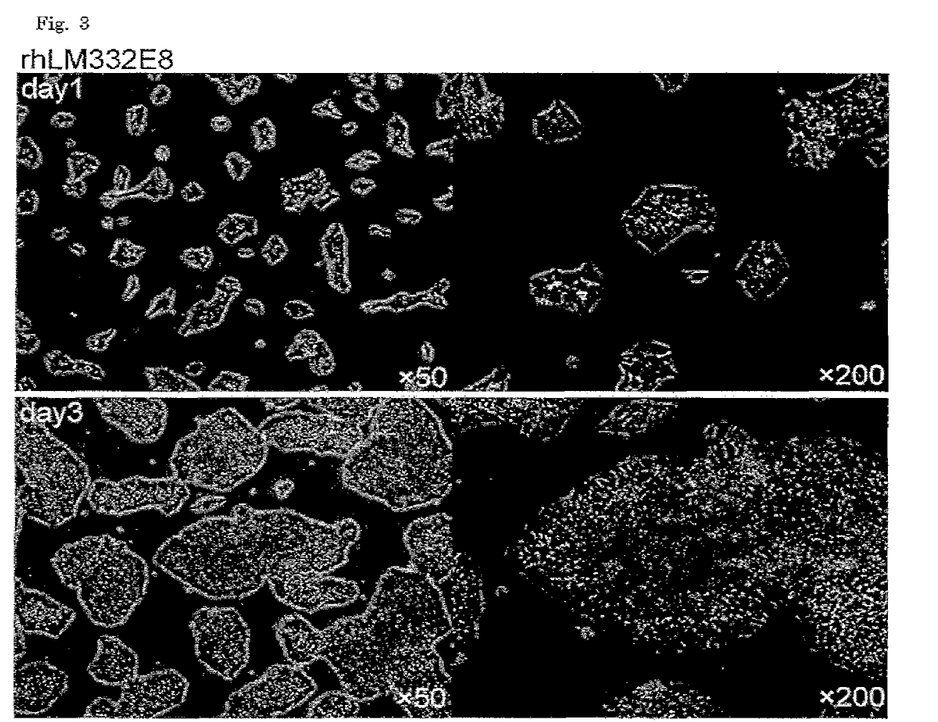
Figure 4:
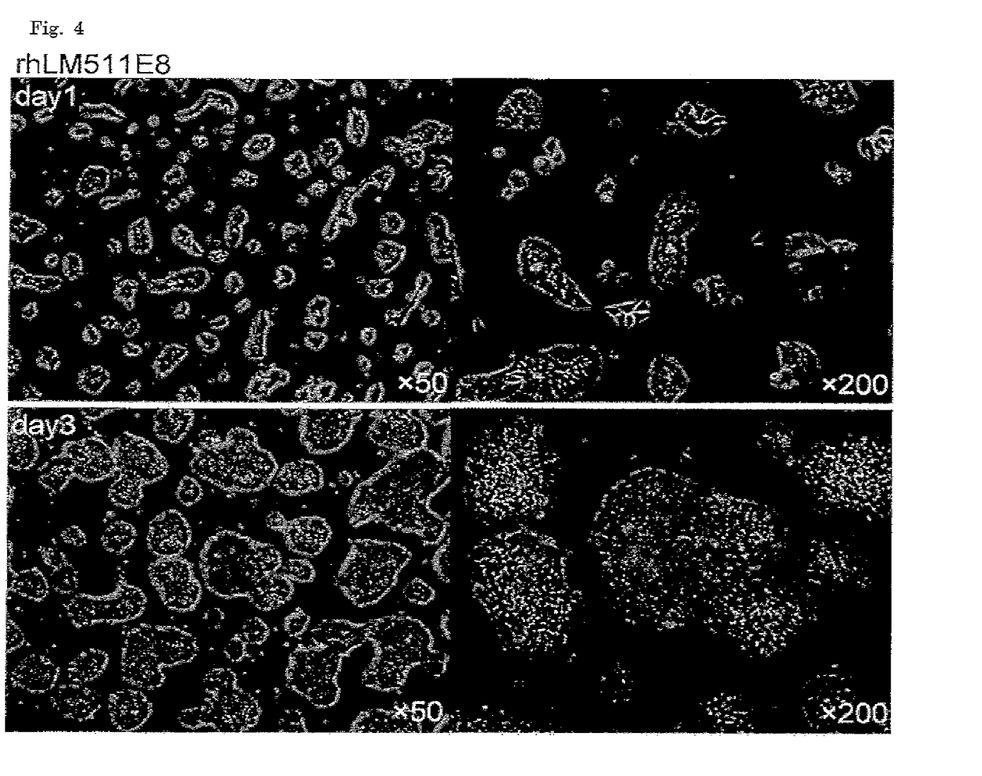
Figure 6:
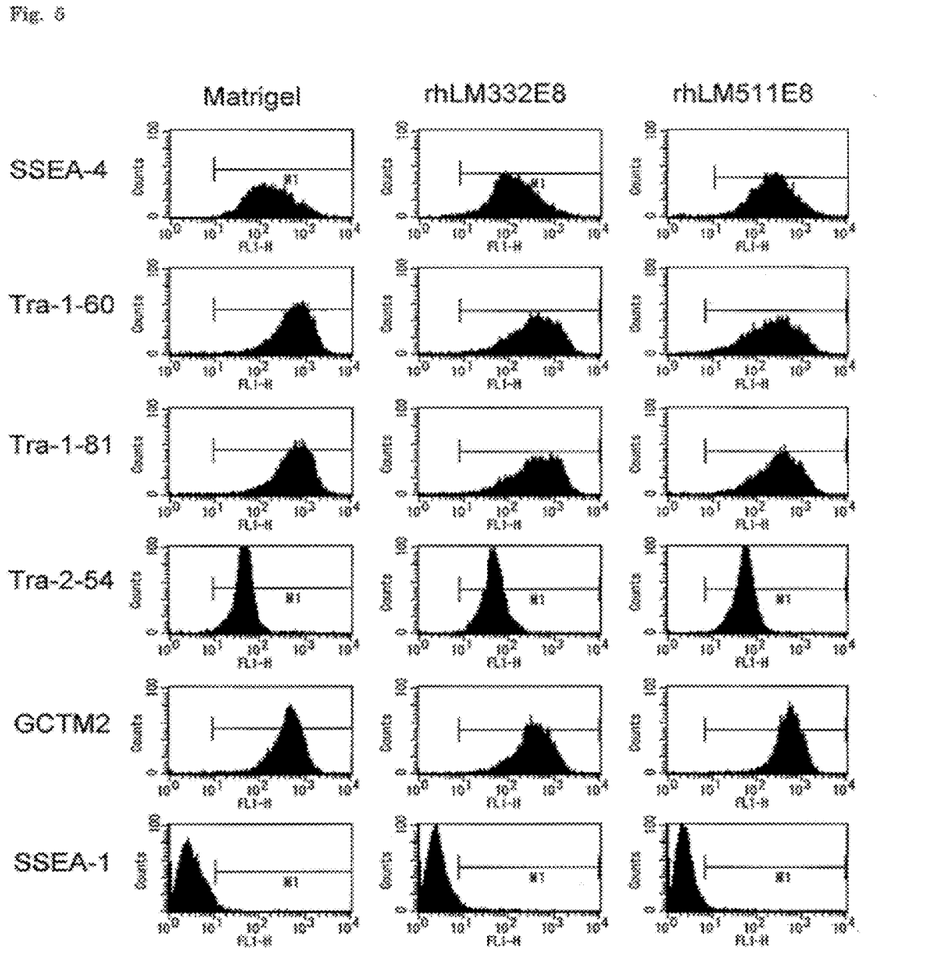

The results of morphological observation of the human ES cells cultured on the dish coated with rhLM332E8 are shown in FIG. 3. The results of morphological observation of the human ES cells cultured on the dish coated with rhLM511E8 are shown in FIG. 4. As is clear from FIGS. 3 and 4, onto the dish coated with rhLM332E8 or rhLM511E8, human ES cells dissociated into single cells attached individually or as a colony re-formed with adjacent cells (see the upper Day 1 sections of FIGS. 3 and 4), and vigorously proliferated afterward (see the lower Day 3 sections of FIGS. 3 and 4). These results demonstrate that a culture substrate coated with rhLM332E8 or rhLM511E8 enables the previously-infeasible single-cell passage culture of human ES cells.

The results of flow cytometric analysis of human ES cell surface antigens are shown in FIG. 5. In FIG. 5, the results of the cells cultured on the dish coated with Matrigel are shown in the left column, the results of the cells cultured on the dish coated with rhLM332E8 are shown in the central column, and the results of the cells cultured on the dish coated with rhLM511E8 are shown in the right column. As is clear from FIG. 5, the results of flow cytometric analysis of surface antigens showed no difference among the cells cultured on the three kinds of dishes: the cells on any of these dishes were highly positive for undifferentiation markers (SSEA-4, Tra-1-60, Tra-1-81, Tra-2-54, GCTM2), but negative for a differentiation marker (SSEA-1). These results demonstrate that a culture substrate coated with rhLM332E8 or rhLM511E8 can maintain undifferentiated state of human ES cells at a level equivalent to that in conventional methods using Matrigel.

The present invention is not limited to the aforementioned embodiments and examples, and various modifications can be made within the scope of the appended claims. Other embodiments obtainable by suitably combining technical means disclosed in different embodiments of the present invention are also included in the technical scope of the present invention. All the academic publications and patent literature cited in the above description are incorporated herein by reference.

---

The invention claimed is:

1. A culture method of human pluripotent stem cells dissociated into single cells in feeder-free culture conditions, comprising the steps of:
dissociating human pluripotent stem cells into single cells, and
culturing the human pluripotent stem cells dissociated into single cells using a culture substrate, the culture substrate being coated with human laminin β5β2γ1 E8 fragment or human laminin α3β3γ2 E8 fragment.

2. The culture method according to claim 1, wherein the coating concentration of human laminin α5β1γ1 E8 fragment or human laminin α3β3γ2 E8 fragment is 0.5 to 25 µg/cm².

3. The culture method according to claim 1, wherein the human pluripotent stem cell are human ES cells or human iPS cells.

4. The culture method according to claim 1, wherein the human pluripotent stem cells dissociated into single cells are seeded at a cell density of $2 \times 10^4$ to $20 \times 10^4$ cells/cm$^2$.

5. The culture method according to claim 1, further comprising forming single-cell-derived colonies through culturing the human pluripotent stem cells dissociated into single cells.

6. The culture method according to claim 1, further comprising maintaining the human pluripotent stem cells in a single-cell state.

7. The culture method according to claim 1, further comprising using a synthetic medium.

\* \* \* \* \*

SEQUENCE LISTING

```
<160> NUMBER OF SEQ ID NOS: 22

<210> SEQ ID NO 1
<211> LENGTH: 26
<212> TYPE: DNA
<213> ORGANISM: Artificial Sequence
<220> FEATURE:
<223> OTHER INFORMATION: Primer Sequence

<400> SEQUENCE: 1
atgatgatga agcttatcga taccgt                                          26

<210> SEQ ID NO 2
<211> LENGTH: 26
<212> TYPE: DNA
<213> ORGANISM: Artificial Sequence
<220> FEATURE:
<223> OTHER INFORMATION: Primer Sequence

<400> SEQUENCE: 2
catcatcatg atatcgaatt cctgca                                          26

<210> SEQ ID NO 3
<211> LENGTH: 29
<212> TYPE: DNA
<213> ORGANISM: Artificial Sequence
<220> FEATURE:
<223> OTHER INFORMATION: Primer Sequence

<400> SEQUENCE: 3
atcatatgga taaagcttat cgataccgt                                       29

<210> SEQ ID NO 4
```

```
<211> LENGTH: 29
<212> TYPE: DNA
<213> ORGANISM: Artificial Sequence
<220> FEATURE:
<223> OTHER INFORMATION: Primer Sequence

<400> SEQUENCE: 4
gtgccagatt atgcagatat cgaattcct                              29

<210> SEQ ID NO 5
<211> LENGTH: 29
<212> TYPE: DNA
<213> ORGANISM: Artificial Sequence
<220> FEATURE:
<223> OTHER INFORMATION: Primer Sequence

<400> SEQUENCE: 5
atccttgtaa tcaagcttat cgataccgt                              29

<210> SEQ ID NO 6
<211> LENGTH: 25
<212> TYPE: DNA
<213> ORGANISM: Artificial Sequence
<220> FEATURE:
<223> OTHER INFORMATION: Primer Sequence

<400> SEQUENCE: 6
gctgccgagg atgctgctgg ccagg                                  25

<210> SEQ ID NO 7
<211> LENGTH: 25
<212> TYPE: DNA
<213> ORGANISM: Artificial Sequence
<220> FEATURE:
<223> OTHER INFORMATION: Primer Sequence

<400> SEQUENCE: 7
ctaggcagga tgccgggcgg gctga                                  25

<210> SEQ ID NO 8
<211> LENGTH: 25
<212> TYPE: DNA
<213> ORGANISM: Artificial Sequence
<220> FEATURE:
<223> OTHER INFORMATION: Primer Sequence

<400> SEQUENCE: 8
cttcagcata gtgctgctga cattg                                  25

<210> SEQ ID NO 9
<211> LENGTH: 27
<212> TYPE: DNA
<213> ORGANISM: Artificial Sequence
<220> FEATURE:
<223> OTHER INFORMATION: Primer Sequence

<400> SEQUENCE: 9
ttacaagcat gtgctataca cagcaac                                27

<210> SEQ ID NO 10
<211> LENGTH: 25
<212> TYPE: DNA
<213> ORGANISM: Artificial Sequence
<220> FEATURE:
<223> OTHER INFORMATION: Primer Sequence

<400> SEQUENCE: 10
```
aatgacattc tcaacaacct gaaag                                          25

<210> SEQ ID NO 11
<211> LENGTH: 25
<212> TYPE: DNA
<213> ORGANISM: Artificial Sequence
<220> FEATURE:
<223> OTHER INFORMATION: Primer Sequence

<400> SEQUENCE: 11
ctagggcttt tcaatggacg gggtg                                          25

<210> SEQ ID NO 12
<211> LENGTH: 34
<212> TYPE: DNA
<213> ORGANISM: Artificial Sequence
<220> FEATURE:
<223> OTHER INFORMATION: Primer Sequence

<400> SEQUENCE: 12
atgatgatgg gcgcgccaag cttatcgata ccgt                                34

<210> SEQ ID NO 13
<211> LENGTH: 25
<212> TYPE: DNA
<213> ORGANISM: Artificial Sequence
<220> FEATURE:
<223> OTHER INFORMATION: Primer Sequence

<400> SEQUENCE: 13
catcatcatg atatcgaatt cctgc                                          25

<210> SEQ ID NO 14
<211> LENGTH: 24
<212> TYPE: DNA
<213> ORGANISM: Artificial Sequence
<220> FEATURE:
<223> OTHER INFORMATION: Primer Sequence

<400> SEQUENCE: 14
gcggccgagg acgcagccaa cagg                                           24

<210> SEQ ID NO 15
<211> LENGTH: 27
<212> TYPE: DNA
<213> ORGANISM: Artificial Sequence
<220> FEATURE:
<223> OTHER INFORMATION: Primer Sequence

<400> SEQUENCE: 15
ggtctagact aagcatcttg ccacacc                                        27

<210> SEQ ID NO 16
<211> LENGTH: 20
<212> TYPE: DNA
<213> ORGANISM: Artificial Sequence
<220> FEATURE:
<223> OTHER INFORMATION: Primer Sequence

<400> SEQUENCE: 16
tgggcgtgga tagcggtttg                                                20

<210> SEQ ID NO 17
<211> LENGTH: 28
<212> TYPE: DNA

```
<213> ORGANISM: Artificial Sequence
<220> FEATURE:
<223> OTHER INFORMATION: Primer Sequence

<400> SEQUENCE: 17
tctgggacag atctgcataa tctggcac                                      28

<210> SEQ ID NO 18
<211> LENGTH: 28
<212> TYPE: DNA
<213> ORGANISM: Artificial Sequence
<220> FEATURE:
<223> OTHER INFORMATION: Primer Sequence

<400> SEQUENCE: 18
agattatgca gatctgtccc agaccaag                                      28

<210> SEQ ID NO 19
<211> LENGTH: 26
<212> TYPE: DNA
<213> ORGANISM: Artificial Sequence
<220> FEATURE:
<223> OTHER INFORMATION: Primer Sequence

<400> SEQUENCE: 19
gcgaattctc acttgcaggt ggcata                                        26

<210> SEQ ID NO 20
<211> LENGTH: 29
<212> TYPE: DNA
<213> ORGANISM: Artificial Sequence
<220> FEATURE:
<223> OTHER INFORMATION: Primer Sequence

<400> SEQUENCE: 20
ggatgctctc atccttatca tcatcatcc                                     29

<210> SEQ ID NO 21
<211> LENGTH: 33
<212> TYPE: DNA
<213> ORGANISM: Artificial Sequence
<220> FEATURE:
<223> OTHER INFORMATION: Primer Sequence

<400> SEQUENCE: 21
gatgatgata aggatgagag catccttaaa aac                                33

<210> SEQ ID NO 22
<211> LENGTH: 29
<212> TYPE: DNA
<213> ORGANISM: Artificial Sequence
<220> FEATURE:
<223> OTHER INFORMATION: Primer Sequence

<400> SEQUENCE: 22
gcgaattctc actgttgctc aagagcctg                                     29
```